United States Patent [19]

Kolodner

[11] 4,455,741
[45] Jun. 26, 1984

[54] FABRICATION OF SOLID STATE ELECTRONIC DEVICES USING FLUORESCENT IMAGING OF SURFACE TEMPERATURE PROFILES

[75] Inventor: Paul R. Kolodner, Maplewood, N.J.

[73] Assignee: AT&T Bell Laboratories, Murry Hill, N.J.

[21] Appl. No.: 434,635

[22] Filed: Oct. 15, 1982

Related U.S. Application Data

[63] Continuation-in-part of Ser. No. 347,783, Feb. 11, 1982, abandoned.

[51] Int. Cl.³ .............................................. H01L 21/66
[52] U.S. Cl. ........................................ 29/574; 374/161
[58] Field of Search ............ 29/574; 250/458.1, 459.1; 374/159, 161

[56] References Cited

PUBLICATIONS

Grilletto, C., "An X-Ray Fluorescence Technique for the Rapid Determination of Phosphorous in PSG Film" in *Sol. State Tech.*, 20(2), 2-1977.

Primary Examiner—Brian E. Hearn
Assistant Examiner—Alan E. Schiavelli
Attorney, Agent, or Firm—Bernard Tiegerman; Bruce S. Schneider

[57] ABSTRACT

Solid state electronic devices are optically monitored during fabrication to detect hot spots which are indicative of faulty operation. The surface temperatures of such a device are measured by applying a fluorescent material to the device, and subsequently monitoring the temperature dependent fluorescence of the material, which is reflective of the temperature of the underlying device. Devices are accepted, rejected, or further processed in response to the monitored fluorescence.

36 Claims, 2 Drawing Figures

FABRICATION OF SOLID STATE ELECTRONIC DEVICES USING FLUORESCENT IMAGING OF SURFACE TEMPERATURE PROFILES

This is a continuation-in-part of U.S. Patent Application Ser. No. 347,783 filed on Feb. 11, 1982 now abandoned.

BACKGROUND OF THE INVENTION

This invention is a technique for forming solid state electronic devices. The technique includes the measurement of surface temperature profiles using fluorescent imaging techniques. The temperature profile of the device may be measured during operation of the device, with a view toward detecting elements operating below specification, as indicated by an abnormal temperature profile.

DISCLOSURES OF INTEREST

The cost of fabricating solid state electronic devices, such as integrated circuit devices, laser diodes, and Josephson junction devices, may be significantly lowered by increasing device yields. One technique for increasing yields centers about detecting faulty devices on the fabrication line with a view toward discarding the devices or correcting them prior to further processing. Current techniques include electrical measurement, with a view toward detecting faulty operation. In many instances, faulty operation of a solid state electronic device will result in unexpected localized hot regions associated with higher than usual power dissipation, and detection of device temperature profiles containing "hot spots" would indicate faulty operation of the device. However, measurement of these temperature profiles is difficult, in part, because of the high spatial and thermal resolution which would be necessary to adequately detect such temperature profiles.

Although little, if any, attempt has been made to detect faulty solid state electronic devices by temperature profile measurement, significant effort has been expended in the measurement of surface temperatures in other areas. Such areas include medical applications, aerodynamic studies, and the monitoring of electrical power generating equipment. Techniques which have been used in such applications include the use of thermocouples, thermistors, or resistance thermometers as sensors which are connected to associated electrical measurement devices.

Recently, optical techniques have been applied to the measurement of temperatures in various commercial environments. Such techniques have included infrared radiometry, dependent in most instances on blackbody emission from a heated surface, optical pyrometry, dependent on the emission of visible radiation from bodies at high temperatures, and the use of phosphors or liquid crystals applied to the surfaces of bodies whose temperatures are to be measured. Phosphor or liquid crystal coatings emit radiation whose spectrum and/or intensity is a function of the temperature of the body to which the coating is applied. However, in many instances, such materials suffer from chemical, physical or optical properties which degrade with time, or which limit the spatial resolution, and temperature range, to which the technique may be applied.

U.S. Pat. Nos. 4,075,493 and 4,215,275, issued to K. A. Wickersheim on, respectively, Feb. 21, 1978 and July 29, 1980, disclose a technique for measuring surface temperatures which includes applying a layer of phosphor material to a body whose temperature is to be measured. When appropriately excited the phosphor material luminesces within two or more wavelength ranges that may be optically isolated from one another, with a relative intensity of emission in these wavelength ranges which vary in a known manner as a function of phosphor temperature. Normalizing the luminescence in one wavelength range to that in the other wavelength range allows for a determination of absolute temperature. The technique, however, is applied to the measurement of relatively large surfaces such as those encountered in medical measurement, wind tunnel testing of models, and the measurement of power generating equipment. Smaller areas may be measured by applying the phosphor to an appropriate optical transmission device such as an optical fiber and using the tip of the fiber as a sensor for spot temperature measurement (see also J. S. McCormack, *Electronics Letters*, 17, 631 (1981)). However, the fiber size limits the spatial resolution of the technique, and the heat capacity of the fiber distorts the observed temperature profile.

SUMMARY OF THE INVENTION

This invention is a method for fabricating solid state electronic devices such as integrated circuits, laser diodes, and Josephson junction devices. In the inventive method such devices are monitored either during or after fabrication so as to detect those which either do not operate, or which operate outside a specified range. Undesirable operation is determined by surface temperature profile measurement of the device, usually during application of appropriate voltages and/or currents to the device.

Surface temperature profiles are measured by applying a thin film of material to the device, which material luminesces when irradiated with appropriate energy. The intensity of the luminescense is dependent upon the temperature of the material, and consequently the luminescence is an accurate measure of the temperature of the underlying device.

The luminescent material is applied to the solid state electronic device as a thin film with thickness less than 5 microns and as small as 300 Angstroms or smaller. Such thin films have associated thermal conductances and heat capacities which are so small that temperature features of sizes less than 1 millimeter, and even as small as, or smaller than, 1 micron may be measured without measurable distortion.

While measurement of the luminescent material may be limited to specific regions of the device, one embodiment of the invention involves imaging the entire device on an appropriate high resolution monitor, such as a CCD camera, so as to obtain a picture of the device with high spatial resolution (less than 1 millimeter and as small as, or smaller than, 1 micron). A "thermal picture" is created by normalizing this image to an image of the device when "cold", i.e., when the device is not powered, so as to remove all optical features, leaving a purely thermal image of high resolution.

The luminescing thin film which is applied to the solid state electronic device should be of sufficient homogeneity so as not to degrade the high resolution which may be obtained in using this technique. As a result, phosphors which comprise particles of crystalline material doped with impurities are likely inappropriate in the inventive technique since the luminescing characteristics of such phosphors vary with the physical characteristics of the material as well as over space, e.g., as a function of grain size. Moreover, the luminescent thin film applied to the device should have a thickness which is smaller than the desired spatial resolution, and preferably no more than half the desired spatial resolution. But because the phosphor particles are typically 10 μm in size, or bigger, sufficiently thin phosphor layers capable of spatial resolutions smaller than, for example, 20 μm, cannot be formed.

Specific embodiments of this invention include the use of Europium TTA and dPMMA dissolved in chlorobenzene and deposited by spinning on the surface of the device. The chlorobenzene solvent evaporates leaving a clear, essentially homogeneous luminescent thin film, comprising Europium TTA distributed homogeneously, even on a microscopic scale (on a scale where dimensions are as small as 0.5 μm), in dPMMA.

DETAILED DESCRIPTION

Figure 1:
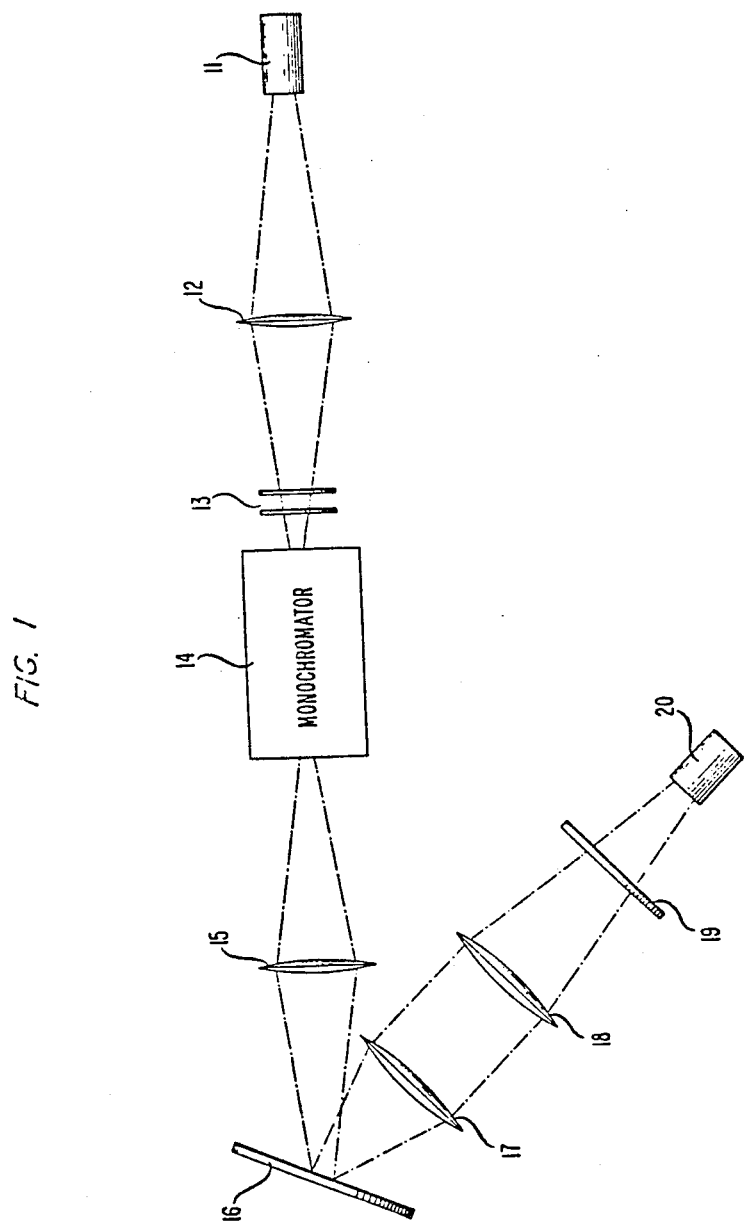
FIG. 1 is a schematic representation of various equipment appropriate to the practice of this invention.

The invention is a method for fabricating solid state electronic devices, such as integrated circuit devices, laser diodes, and Josephson junction devices. According to the inventive process, the temperature profile of the device is measured during fabrication so as to detect those devices which do not meet operating specifications. Since operation of the device results in a characteristic temperature profile, operating parameters which are outside of a specified range are detected by associated uncharacteristic temperature profiles.

In the inventive technique the fabrication of the device proceeds as in the prior art with, however, the additional step of applying to the surface of the device an appropriate thin film of material which fluoresces upon exposure to specified forms of energy. The material is referred to as fluorescent, or sometimes as luminescent, in accordance with common usage, and indicating that such materials will radiate electromagnetic energy upon exposure to appropriate energy. For example, such materials, upon exposure to UV radiation (having a wavelength ranging from about 2000 Angstroms to about 4000 Angstroms), may be excited, and upon de-excitation will emit UV, visible (wavelength ranging from about 4000 Angstroms to about 7000 Angstroms) or infrared (wavelength ranging from about 7000 Angstroms to about 10,000 Angstroms) radiation. The thin film of material which is applied to the solid state electronic device is fluorescent or luminescent in this sense.

The practice of the invention is independent of the specific nature of the solid state electronic device. However, to place the significance of this invention in its proper perspective, it may be helpful to indicate that the specific devices to which the invention is applied will usually have physical features less than 300 microns in extent and oft times less than 5 microns in extent. Leading edge technology will include devices, for example, integrated circuit devices, with physical features less than 1 or one-half micron. Associated with these devices will be regions of limited extent where power is dissipated, thereby elevating the temperature of the surface of the device. Such power dissipation regions such as, e.g., gate channels of an integrated circuit device, may be less than one hundred microns in extent, in at least one dimension. Temperature profiles may vary, however, across regions less than 20 microns. In the practice of this invention, temperature variations of less than ten, one, one-tenth, and even one-hundredth of a degree Celsius, and temperature profiles with spatial resolutions smaller than 50 microns, 10 microns, and even 1 micron, have been measured.

When measurement techniques with high thermal and spatial resolution are being considered, the thermal effect of the fluorescent layer deposited on the device becomes significant. So, for example, if the heat capacity of the fluorescent layer is relatively large, the layer itself will distort the observed temperature profile. Consequently, one of the significant features of the fluorescent materials employed in the invention is that they are deposited with thicknesses less than 10 or 5 microns, and are most usually deposited with thicknesses less than 1 or 0.5 microns. Prior art techniques have involved the use of fluorescent layers deposited on surfaces, and the measurement of surface temperatures using fluorescent techniques. However, by the nature of such prior art materials, only relatively thick layers, i.e., layers having thicknesses greater than about 10 microns, could be deposited and consequently either the spatial or thermal resolution of those prior art techniques were limited. For example, a prior art layer of material having a thickness of about 10 microns could not, in principle, provide a spatial resolution smaller than about 20 microns and, in practice, typically had a spatial resolution of no better than about 100 microns.

Yet another significant feature of the fluorescent materials employed in the inventive fabrication method is that upon irradiation by appropriate energy such as, for example, UV light, the material will fluoresce with an intensity characteristic of the temperature of the underlying device. A relative or absolute temperature profile of the surface of the device is obtained by measuring this emitted fluorescence. The absolute temperature is obtained by comparing the fluorescence produced when the device is, for example, powered, and thus emitting heat, to the fluorescence produced at a known temperature when the device is not emitting heat. The inventive technique, however, is more concerned with the relative temperature profile than it is with the absolute temperature, although it may be applied to the measurement of the absolute temperature as well.

Included among the fluorescent materials employed in the inventive fabrication method, and which exhibit the two significant features described above, are two Europium-containing materials: Europium Thenoyltrifluoroacetonate (EuTTA); and perdeutero-(tris-6,6,7,7,7,8,8-heptafluoro-2,2-dimethyl-3,5 octanedionate) Europium (EuFOD). As used in the invention, each of these Europium-containing materials is incorporated into a polymer which is deposited onto a device surface by co-dissolving the polymer and the Europium compound in an appropriate solvent, and then spinning the resulting solution onto the device surface. The solvent evaporates during the spinning step, leaving a thin film of polymer homogeneously doped (if there are crystallites in the film are small, typically about 1 μm in size, or smaller, and spaced apart by hundreds of microns) with one of the Europium-containing materials.

The EuTTA, as used in the invention, is incorporated into, for example, perdeutero-poly (methylmethacrylate) (dPMMA), the EuTTA-doped dPMMA being deposited onto a device surface (using the general procedure described above) as a film having a thickness ranging from about 0.01 to about 5 μm. Moreover, the EuTTA constitutes about 0.5 to about 40 percent by weight of the film (and thus the dPMMA constitutes about 60 to about 99.5 percent by weight of the film), the preferred amount of EuTTA being about 40 percent by weight. Films having thicknesses less than about 0.01 μm are undesirable because they contain insufficient fluorescent material to produce an easily detectable fluorescence, while films having thicknesses greater than about 5 μm result in undesirably low thermal spatial resolutions. In addition, films (even relatively thick films) whose EuTTA content is less than about 0.5 percent by weight are undesirable because their fluorescence is too small to be easily detected, while an EuTTA concentration greater than about 40 percent by weight is undesirable because the EuTTA crystallizes out of solution during spinning, resulting in an inhomogeneous, often useless, film.

The EuTTA-doped dPMMA films described above are formed on a device surface by co-dissolving, in the above relative proportions, the EuTTA and dPMMA in a solvent such as chlorobenzene or methylethylketone (MEK). The resulting solution is then filtered in order to remove EuTTA microcrystals and dust particles (which might nucleate crystallization of EuTTA), and spun onto the device surface. The resulting film thickness is roughly proportional to the total concentration by weight of the EuTTA and dPMMA in the solvent, and roughly inversely proportional to the spin speed, which typically ranges from about 400 to about 10,000 rpm. For example, if the total concentration of the EuTTA and dPMMA in chlorobenzene is about 3 percent by weight, then spin speeds ranging from about 400 rpm to about 10,000 rpm yield films whose corresponding thicknesses range from about 4,000 Angstroms to about 100 Angstroms. In general, control samples are used to determine the appropriate concentrations and spin speeds which yield the desired film thicknesses.

It should be noted that while EuTTA is preferably incorporated into the deuterated PMMA polymer (the dPMMA), non-deuterated PMMA or other polymers, e.g., polyacrylic acid, are also useful.

The EuFOD, as used in the invention, is incorporated into a polymer, for example, a glass resin sold under the trade name GR650 glass resin by the Owens-Illinois Corporation of Midland, Mich. The EuFOD-doped glass resin is deposited onto a device surface (by spinning a solution containing the EuFOD and the glass resin) as a film having a thickness ranging from about 0.01 to about 5 μm. Moreover, the EuFOD constitutes about 2 to about 50 percent by weight of the film (and thus the glass resin constitutes about 50 to about 98 percent by weight of the film), the preferred amount of EuFOD being about 50 percent by weight. Films having thicknesses and EuFOD concentrations outside the above-specified ranges are undesirable for the reasons given above.

The EuFOD-doped glass resin films described above are formed on a device surface by co-dissolving, in the above proportions, the EuFOD and glass resin in a solvent such as MEK. The resulting solution is then filtered (to remove microcrystals and dust particles) and spun onto the device surface at a speed ranging from about 400 rpm to about 10,000 rpm. As before, the resulting film thickness is roughly proportional to the total concentration by weight of the EuFOD and glass resin, and roughly inversely proportional to the spin speed. For example, if the total concentration of the EuFOD and glass resin in MEK is about 20 percent by weight, then spin speeds ranging from about 400 rpm to about 10,000 rpm yield films whose corresponding thicknesses range from about 2 μm to about 700 Angstroms. As before, control samples are used to determine the appropriate concentrations and spin speeds which yield the desired film thickness.

With regard to the temperature dependence of the fluorescence of the Europium-containing materials, a semi-log plot of the fluorescence intensity of EuTTA-doped dPMMA, as a function of temperature, is approximately a straight line having a slope of about $-0.05$/degree Celsius. This relationship holds over temperatures ranging from about 10 degrees Celsius to about 60 degrees Celsius. Similarly, a semi-log plot of the fluorescence intensity of the EuFOD-doped glass resin, as a function of temperature, is also approximately a straight line having a slope of about $-0.04$/degree Celsius. This latter relationship also holds over temperatures ranging from about 10 degrees Celsius to about 60 degrees Celsius. It should be noted that the Europium-containing materials are still useful outside the above-specified temperature ranges, although the temperature dependence of these materials may be different.

While the radiation emitted from only limited areas of a solid state electronic device may be measured, an embodiment of the invention involves the measurement of large areas of the device using an appropriate imaging technique so as to obtain a "thermal picture" of the device. It is conceivable that in commercial application most desirable embodiments would involve the limited "thermal sampling" of only a specific region of the solid state electronic device, and it is clear that the invention encompasses such an application. However, the discussion in the Example, below, is in terms of imaging large areas of a device. Likewise, simple measurement of the "heated", i.e., powered, device may be made, or alternatively the measurement may be normalized to the "cold", i.e., unpowered, device, thereby removing effects due to optical features and leaving a purely thermal image of higher resolution.

The inventive fabrication method also includes the use of both steady (with respect to time) and non-steady thermal imaging techniques. In the steady imaging technique, a solid state electronic device (or a portion of the device) is powered so as to produce a generally steady dissipation of heat, while the fluorescent film of material covering the device is exposed to a generally steady source of fluorescence-inducing energy. In the non-steady imaging technique, either the device (or a portion of the device) is powered so as to produce a transient or time-varying dissipation of heat, or the fluorescent material is exposed to a non-steady source of energy, or both. One specific embodiment of the non-steady thermal imaging technique, denoted here as the pulsed thermal imaging technique, provides enhanced thermal spatial resolution by minimizing the adverse effects (with respect to resolution) of thermal diffusion.

When a component of a solid state electronic device is powered, the heat given off by the component diffuses, i.e., is conducted, through the surrounding materials, e.g., metal, and semiconductor material, producing an increase in the apparent size of the device component generating the heat, as inferred from a thermal image of the device. For example, a material such as silicon has a thermal diffusivity of about 1 cm²/sec. Thus, for example, if a (hypothetical) delta-function heat pulse were to be delivered to the silicon from a (hypothetical) infinitesimally thin, powered device component, then after just 10 nanoseconds, thermal diffusion will have produced a temperature profile having a width of about 1 μm. Therefore, in order to achieve a thermal spatial resolution of 1 μm or smaller, a thermal image should be made with a resolution in time which is smaller than the time required for heat to diffuse 1 μm in the silicon, i.e., a time resolution of about 10 nanoseconds or less. Such a time resolution is achievable with a fluorescent material only if the fluorescence lifetime of the material, i.e. the time required for a detectable change in fluorescence intensity in response to a sudden change in temperature or illumination, is equal to, or less than, about 10 nanoseconds. If the fluorescence lifetime of the material is greater than 10 nanoseconds, then even if the fluorescent material is strobed with, for example, a nanosecond pulse of energy coincident with a nanosecond pulse of power delivered to the device, the resulting thermal image (of the temperature profile produced by the power pulse) will be distorted because the detected fluorescence will constitute the response to the temperature profile of the device integrated over the fluorescence lifetime. That is, the width of the temperature profile will have broadened because of thermal diffusion during the fluorescence lifetime of the material.

In accordance with the pulsed thermal imaging technique employed in one embodiment of the invention, a preselected thermal spatial resolution, x, is achieved in thermally imaging a device by depositing a film of fluorescent material onto the surface of the device. The deposited material should exhibit both a temperature-dependent fluorescence, and have a fluorescence lifetime, $\tau$, which is less than $t_x$, the time required for heat to diffuse across the surface of the device by a distance equal to the preselected thermal spatial resolution, x. In order that the film appear isothermal, the film should be sufficiently thin that heat diffuses through its thickness in a time much less than $t_x$. Thus, the thickness of the film is less than x, and preferably less than one-twentieth of x.

A transient in the thermal profile of the device is then produced by delivering power to the device, e.g., by applying a voltage and/or current source to the device, or by increasing the power being delivered to the device. Preferably, the power, or the increase in power, is delivered as a pulse having a duration less than $t_x$. Substantially simultaneously with the transient in the thermal profile, the fluorescent material covering the device is strobed with a pulse of fluorescence-inducing energy, e.g., a pulse of UV light, of duration less than $t_x$, and the resulting fluorescence is detected. Alternatively, the fluorescent material is continuously exposed to fluorescence-inducing energy, and a detector is gated, i.e., exposed to the fluorescence, for a time period less than $t_x$, substantially simultaneously with the onset of the thermal transient. Here, the term "substantially simultaneously" denotes that the time interval between the onset of the thermal transient and the strobing or gating is less than $t_x$. Because the fluorescence lifetime, $\tau$, of the material is less than $t_x$, the fluorescence intensity of the material will change in response to the thermal transient in a time less than $t_x$, and thus it is possible to achieve the desired thermal spatial resolution, x.

It should be noted that in a variation of the pulsed thermal imaging technique, encompassed by the invention, either the strobing or the gating is performed at a preselected time interval after the onset of the thermal transient, rather than substantially simultaneously with the onset of the transient.

By way of illustration, if a thermal spatial resolution of 1 μm is desired in thermally imaging a device which consists largely of silicon (whose thermal diffusivity is about 1 cm²/sec), then a fluorescent material having a fluorescence lifetime, $\tau$, less than about 10 nanoseconds (heat will diffuse about 1 μm through silicon in 10 nanoseconds), is deposited onto the device. The thickness of the fluorescent material is preferably less than 0.05 μm. Power is then delivered to the device, and the fluorescent material is, for example, substantially simultaneously strobed with a pulse of energy having a duration less than 10 nanoseconds. The detected fluorescence of the material will yield a temperature profile of the device with a thermal spatial resolution of about 1 μm, and will thus reveal the locations of the sources of heat with a resolution of about 1 μm or less.

Included among the temperature-sensitive fluorescent materials which exhibit fluorescence lifetimes of about 10 nanoseconds or less, and which are usefully employed in the pulsed thermal imaging technique to measure temperature profile with thermal spatial resolutions of 1 μm or less (assuming the thermal diffusivity of the device is about 1 cm²/sec) is polyethyleneimine doped with Rhodamine B. In use, the Rhodamine B-doped polyethyleneimine is deposited onto a device surface as a film having a thickness ranging from about 0.01 to about 5 μm, with the concentration of the Rhodamine B being about 0.5 to about 25 percent by weight of the film (and thus the polyethyleneimine constitutes to about 75 to about 99.5 percent by weight of the film). The preferred concentration of the Rhodamine B is about 25 percent by weight. Film thicknesses and Rhodamine B concentrations outside the above-specified ranges are undesirable for the same reasons as those given above.

The Rhodamine B-doped polyethyleneimine films described above are formed on a device surface by co-dissolving, in the above proportions, the Rhodamine B and polyethyleneimine in a solvent such as MEK. The resulting solution is then filtered and spun onto a device surface. Again, the resulting film thickness is roughly proportional to the total concentration by weight of the Rhodamine B and polyethyleneimine in the solvent, and roughly inversely proportional to the spin speed. For example, if the total concentration by weight of the Rhodamine B and polyethyleneimine in the solvent is about 7.5 percent, then spin speeds ranging from about 400 rpm to about 10,000 rpm yield films whose corresponding thicknesses range from about 1 μm to about 300 Angstroms. As before, control samples are used to determine the appropriate concentrations and spin speeds which yield the desired film thickness.

Over temperatures ranging from about 10 to about 40 degrees Celsius, a semi-log plot of the fluorescence intensity of Rhodamine B-doped polyethyleneimine, as a function of temperature, is approximately a straight line having a slope of about −0.03/degree Celsius.

Other temperature-sensitive fluorescent materials which exhibit fluorescence lifetimes of about 10 nanoseconds or less, include bianthrone, dimethylaminoazobenzene, and 9-methylanthracene. These materials, rather than being deposited by spinning, are deposited by conventional vacuum sublimation techniques in layers having thicknesses ranging from about 0.01 to about 5 μm. Thicknesses outside this range are undesirable for the same reasons as those given above. Over temperatures ranging from about 10 to about 60 degrees Celsius, a semi-log plot of the fluorescence intensity of each of these materials, as a function of temperature, is approximately a straight line having a slope of about −0.02/degree Celsius, −0.01/degree Celsius, and −0.025/degree Celsius, respectively.

Other materials can be useful in the practice of the invention. These materials, which exhibit temperature-dependent fluorescence, are characterized by the fact that when a particular (unpopulated) quantum level is populated, depopulation (relaxation) occurs both radiatively (the material fluoresces) and through a temperature-dependent, non-radiative pathway. The rate at which relaxation occurs radiatively largely determines the fluorescence lifetime of the material. Moreover, the quantum efficiency of the fluorescence, and thus the fluorescence intensity, is a function of both the radiative and (temperature-dependent) non-radiative relaxation rates, and thus the fluorescence intensity is temperature dependent.

Materials having the above characteristics typically exhibit two (unpopulated) quantum levels, the second quantum level being at a higher energy level than the first. When the first quantum level is populated, depopulation occurs both radiatively and by a temperature dependent transfer of energy to the second, higher energy quantum level. The second quantum level is depopulated by a fast (compared to the radiative depopulation rate of the first level), nonradiative relaxation.

On the molecular level, the materials which exhibit temperature dependent fluorescence consist of a single molecule, or two or more molecules chemically bonded together. One group of materials which (at the molecular level) includes, for example, two chemically bonded molecules, is typified by one of the molecules having a triplet level and the other molecule having a lower emission level into which energy is transferred from the triplet level. In addition, one of the two molecules typically has a relatively high absorption level from which energy is transferred into the triplet level and into the emission level.

By exposing the material to appropriate energy, e.g., UV light, the absorption level is populated. Energy in the absorption level is transferred into the triplet level, and is in turn transferred into the emission level. Alternatively, the energy is transferred directly from the absorption level to the emission level. The emission level is then depopulated by an emission of radiation, i.e., the material fluoresces, and by a temperature dependent transfer of energy back to the triplet level. In order that the material exhibit useful, temperature sensitive fluorescence, the energy gap between the triplet and emission levels should be relatively large, e.g., 1000 $cm^{-1}$, and the rates of energy transfer into and out of the triplet level should be relatively fast, e.g., energy transfer times should be as small as a few nanoseconds, or smaller.

EXAMPLE

The rare-earth chelate Europium Thenoyltrifluoroacetonate (EuTTA) (Eastman No. 8990) is known to have a fluorescence quantum efficiency which decreases monotonically with temperature, due to a thermal activation from the fluorescing $Eu^{3+}$ $5D_0$ level to a radiationlessly deactivated triplet level in the TTA ligand. The TTA absorbs strongly in a wide band centered at 345 nm, which is conveniently pumped by a Hg arc lamp or by a UV $Ar^+$ laser. The ligand excitation is transferred to the $Eu^{3+}$ ion, causing fluorescence from the $Eu^{3+}$ $5D_0$ level in a narrow line at 612 nm. The fluorescence quantum efficiency in cold solutions approaches 60 percent.

In the experiments described here, the EuTTA was incorporated into a polymer film spun onto the sample. A drop of a filtered chlorobenzene solution containing 1.2 percent by weight EuTTA and 1.8 percent by weight perdeutero-poly-(methylmethacrylate) (dPMMA) was placed on an integrated circuit sample, which was then spun at 600 rpm until dry and baked in vacuum at 130 degrees Celsius for 30 minutes. A typical film formed in this manner is ∼300 nm thick (∼3.5 optical absorption depths at 364 nm, but transparent in the visible), and exhibits bright, microscopically uniform fluorescence under UV excitation. A semi-log plot of the fluorescence intensity as a function of temperature is a straight line of slope −0.05/degree Celsius. This behavior extends from well below room temperature to at least 60 degrees Celsius. Films made with the more readily available hydrogenated PMMA exhibit a temperature dependence weaker by a factor of about 2. The fluorescence appears to be unaffected by electric fields. In this experiment, we record an image of the fluorescence produced in a EuTTA/dPMMA film on a heated surface (in this case, a powered Si MOSFET device on an integrated circuit chip). To remove optical contrast not associated with the temperature profile, we normalize this image against one made with no heating (i.e., sample at uniform, ambient temperature). We find that this process removes all optical features, leaving a purely thermal image of high resolution.

The optical arrangement is shown in FIG. 1. Light from a 100 W Hg arc lamp, 11, is passed through a lens, 12, blue-glass filters, 13, and a 0.25 m monochromator, 14, and is brought to a focus on the sample, 16, at an oblique angle using lens, 15. The exit slit of the monochromator is removed, causing uniform illumination of the sample at an intensity of 700 $\mu W/cm^2$ in a wavelength band 345–380 nm, as measured with a calibrated photodiode. (The monochromator is unnecessary, but it was convenient to leave it in an existing optical set-up.) Using two camera lenses, 17 and 18, and a 612 nm interference filter, 19, the speciment is imaged with magnification 4.4 onto a CCD camera chip, 20. The CCD, Fairchild Model 202, consists of a rectangular, 100×100 array of photodiodes on 30 μm×40 μm centers; the short dimension of each resolution element (pixel) in the sample image is thus 6.8 μm. Weak digital filtering in the final images (a 1.5-pixel HWHM convolution) degrades the real resolution element size to 14 μm×18 μm HWHM; i.e., to about 15 μm. The quantum efficiency of the CCD is 0.35 at 612 nm.

The Fairchild 202 CCD is an interline transfer device which needs no shutter. The chip is clocked out by a hard-wired sequencer which reads alternate odd-even row half-frames. The camera is controlled by an LSI-11/23 microcomputer which writes images onto a floppy disk. Offline image processing is performed with a similar computer with more memory and a 256×256 pixel color display. The present camera sequencer was designed for long exposures and has a minimum exposure time of 5 seconds, although this could certainly be shortened. The excitation UV intensity was adjusted so that, with this exposure, the brightest pixels in the image registered nearly full scale, or roughly 3500 "A/D units" (ADU's). 1 ADU corresponds to 25 photoelectrons; thus if we spatially average over 4×4 (FWHM) groups of pixels and add up 8 exposures, the total signal-to-shot-noise ratio should be $[3500 \times 25 \times 8 \times 4^2]^{\frac{1}{2}} = 3300$. This, in fact, matches our observed noise level. Shot noise dominates all other noise sources here, so this determines our temperature resolution: $[3300 \times (0.05/\text{degrees Celsius})]^{-1} = 0.006$ degrees Celsius. This can be imprved by simply collecting more photons. All images discussed here were made with 5 second exposures at 700 $\mu W/cm^2$ input intensity.

Figure 2:
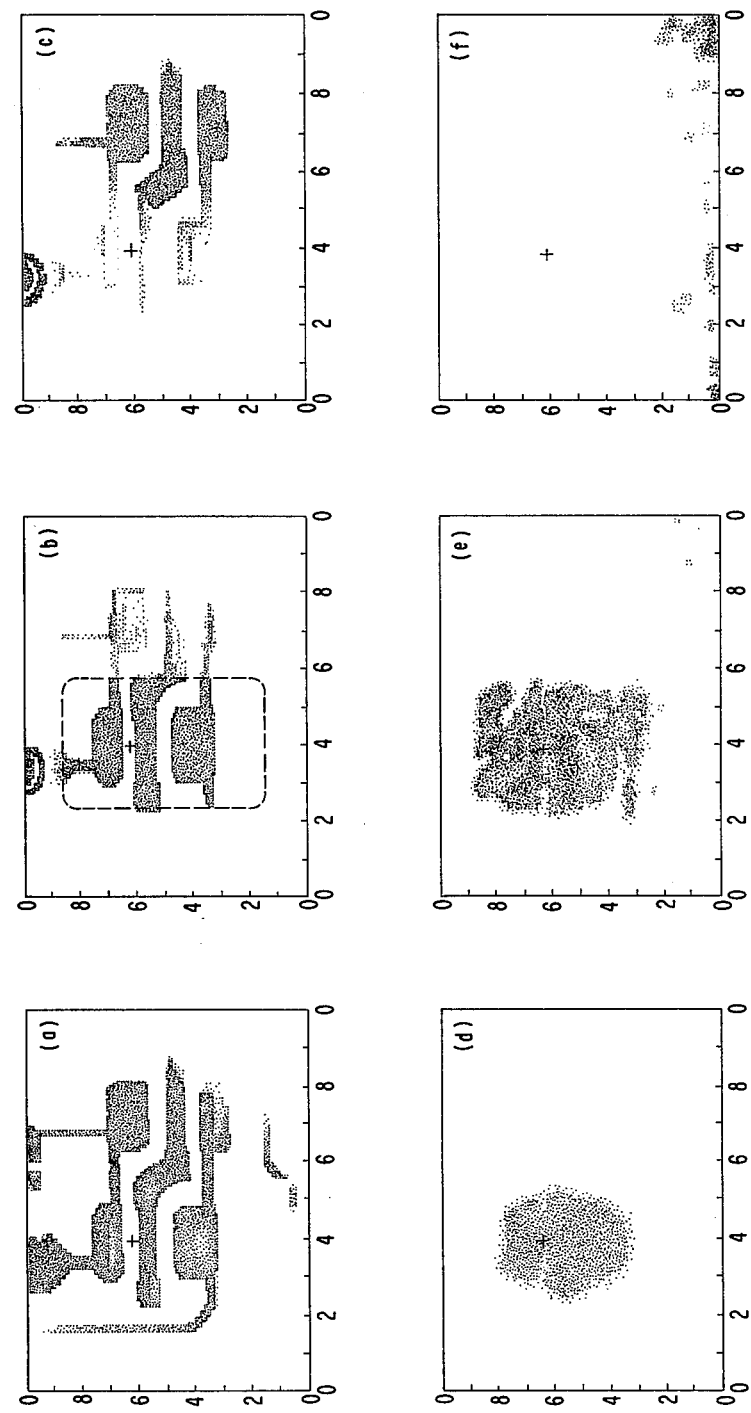
FIG. 2 illustrates reproduction of various thermal images of integrated circuit devices which were taken using the inventive process.

The integrated circuits we examined were high-power series 2 GDX MOSFET devices in a packaged IC chip. A reproduction of a fluorescence image of a pair of these devices, wired in antiparallel, is shown in FIG. 2a. The spatial resolution here and in FIGS. 2b and 2c is just under 10 $\mu$m. The three stippled horizontal stripes are 1.5 $\mu$m thick metallizations laid over the anode (thin; top left and bottom right), cathode, (wide; bottom left and top right) and gate (center) of both devices. With the gates floating, the MOSFET pair acts as antiparallel diodes connecting the upper and lower metallizations. Each device sits in a separate, 50 $\mu$m deep "tub" of single-crystal Si set flush with the surface of the polycrystalline Si substrate (the left-hand tub is outlined in dashed lines in FIG. 2b). The horizontal dimensions of the tubs are 300 $\mu$m × 480 $\mu$m. They are electrically and thermally insulated on all sides by a 3.5 $\mu$m thick lining of $SiO_2$.

The reproduced image in FIG. 2a (the "cold" image) was made with both devices off. The metallized regions of the actual image were about 2 times brighter than their surroundings; this was due only to the higher optical reflectivity of the metal. When 3.1 V of the appropriate polarity is applied between the upper and lower metallizations, 60 mA of current is driven through the device on the left, causing heating by 190 mW. This results in a localized darkening of the image, due to thermal quenching of the fluorescence and centered on the left-hand device, which is dramatically evident to the naked eye. To demonstrate this, we subtracted the resulting "hot" image from the "cold" image reproduced in FIG. 2a; the result is shown in FIG. 2b. In the convolution of thermal and optical images, the hot device on the left appeared dramatically brighter. In a similarly reproduced image with the electrical polarity reversed, FIG. 2c, it is the right-hand device which conducts the current, gets hot, and appears brighter. The image brightness was proportional to the logarithm of the light intensity incident on the CCD. The contrast was enhanced by digital "windowing" (background subtraction) and "stretching" (brightness enhancement).

In order to remove the spatial variations in fluorescence intensity present even in isothermal images such as those reproduced in FIG. 2a, we digitally "divided" the "hot" and "cold" images to produce an image reproduced in FIG. 2d. That is, the brightness of each pixel in the original image, reproduced in FIG. 2d, was proportional to the logarithm of the ratio of the brightness of that pixel in the "cold" image to that in the "hot" image and is thus proportional to the temperature difference there. This normalization procedure removes all traces of spatial brightness variations due to the optical properties of the fluorescent film, the specimen, the optics, and the CCD, leaving a purely thermal image.

The procedure is carried out offline by a computer program which performs the sequence of picture operations $$\left\{ \left[ S \sum_i (C_i - B) \right] / \left[ S \sum_i (H_i - B) \right] - 1 \right\} ,$$

where $C_i$ and $H_i$ are the "cold" and "hot" images, B is a bias image (taken with the arc lamp blocked), and S is the 1.5-pixel-HWHM convolution operation. The convolution is necessary to remove artificial high-spatial-frequency noise associated with F202 mask geometry, and it degrades our spatial resolution to 15 $\mu$m HWHM. Program execution time on the LSI-11/23 is less than one minute. We typically use two each of the "hot" and "cold" images in the program; thus five images in total are used to produce each thermal image. Automated windowing and stretching are used for contrast enhancement in all the images.

First examination of the original image reproduced in FIG. 2d revealed that power dissipation in the highly conductive but insulator-lined tub on the left caused its surface to heat up fairly uniformly, by about 7 degrees Celsius. The edges of the image heated up by about 5 degrees Celsius, due to lateral heat conduction through the substrate. Further examination of this and other images made at lower power levels revealed several details. First, the metallizations are hotter than the rest of the tub surface. Because of their thinness, the metallizations present essentially no thermal impedance normal to the device surface, but they conduct very little heat laterally, either across the tub boundaries or within them. Thus, the brightness of the metallizations in the original thermal image drops abruptly at the tub boundaries. A similar thermal boundary extends in a horizontal line across the center of the cathode (lowest metallization on the left-hand device). Because of the poor lateral thermal conductance of the metallizations, the thermal image is not blurred and presents an accurate picture of where the heat is dissipated: in the resistive diffusions below the anode and the top half of the cathode, and in the constricted channel below the gate. Heating extends the full width of each diffusion but is minimal in the intrinsic region between the anode and the gate.

We have found that, at high device power levels, a small amount of Si recombination radiation, in the wavelength region 0.86–1.0 $\mu$m, leaks through our interference filter and is recorded, along with the fluorescence, by the CCD camera. Quantitative measurements reveal that this caused a slight but insignificant distortion of the image reproduced in FIG. 2d, but it had negligible effect on the rest of the images reproduced in FIG. 2.

To establish the sensitivity of this technique, we made thermal images of the left-hand device while it dissipated only 4.8 mW. In this case, the darkening of the fluorescence is not visible to the naked eye. Two such images were summed (8 exposures total) to produce the image reproduced in FIG. 2e. Here, contrast was again enhanced by automatic windowing and stretching. Once again, the tub heats up much more than the edges of the image. The geometry of the image is the same as at higher power levels. The background level near the cold edges of the image was typically 4100 ADU, while the peak of the hot spot experiences a 23 ADU increase over that background, corresponding to a peak temperature rise of $$[(4100/23) \times (0.05/\text{degrees Celsius})]^{-1} = 0.11 \text{ degrees Celsius}.$$

This is consistent with the level of dissipated power. To assess our noise level, we subtracted the two images which were added to produce the image reproduced in FIG. 2e; the result is reproduced in FIG. 2f. This noise pattern has no systematic spatial structure, and the standard deviation of the brightness is about 2 ADU. Thus, our signal-to-noise ratio is about 11, corresponding to a temperature resolution of 0.01 degrees Celsius, in agreement with the shot-noise calculation above. Using this procedure, we observed that our temperature resolution decreases by a factor 2 when we decrease our collected light level by a factor 4. Thus, our temperature resolution is limited only by shot noise and can be improved just by collecting more light. This can be done by digitally co-adding sequential images up to 64,000 ADU/pixel, in order to avoid CCD saturation.

The spatial resolution in this experiment, 15 $\mu$m HWHM, is determined mostly by the 1.5-pixel convolution step in the digital image processing. With a different camera, this could be deleted with no loss in resolution. However, examination of unconvolved thermal images reveals an intrinsic 25 $\mu$m–30 $\mu$m thermal gradient scale length in these MOSFET devices, so that the 1.5-pixel convolution does not seriously degrade our resolution in these thermal images. Nonetheless, these considerations imply that 1 $\mu$m spatial resolution is possible, with the use of a high-power microscope and the proper CCD camera. Such a system could fully resolve the temperature profile in a Si device switched at 5 MHz, in which the thermal diffusion length is 3 $\mu$m. To obtain 0.01 degrees Celsius resolution with the same exposure times as used here would require a UV illumination level of $\lesssim$25 mW/cm$^2$, still very low compared to device dissipation levels.

What is claimed is:

1. A method for fabricating a solid state electronic device, comprising the steps of:
   forming a layer of fluorescent material on a surface of a partially or fully completed solid state electronic device, the fluorescence of said material varying as the temperature of the underlying device varies;
   exposing said material to energy which causes said material to fluoresce;
   monitoring the fluorescence of said material while the solid state electronic device is contacted with a voltage and/or current source; and
   accepting, rejecting, or further processing said device in response to the monitored fluorescence.

2. The method of claim 1 wherein said layer of material is less than 10 microns thick.

3. The method of claim 2 wherein said layer of material is less than 5 microns thick.

4. The method of claim 3 wherein said layer of material is less than 1 micron thick.

5. The method of claim 1 wherein the fluorescence of said material is detectably responsive to temperature changes less than 10 degrees Celsius.

6. The method of claim 5 wherein the fluorescence of said material is detectably responsive to temperature changes less than 1 degree Celsius.

7. The method of claim 6 wherein the fluorescence of said material is detectably responsive to temperature changes less than a tenth of a degree Celsius.

8. The method of claim 7 wherein the fluorescence of said material is detectably responsive to temperature changes less than a hundredth of a degree Celsius.

9. The method of claim 1 wherein the spatial resolution of the thermal profile associated with the monitored fluorescence is less than 50 microns.

10. The method of claim 9 wherein the spatial resolution of the thermal profile associated with the monitored fluorescence is less than 2 microns.

11. The method of claim 1 wherein the energy which causes the material to fluoresce is ultraviolet light in the spectral range of 300 to 400 nanometers.

12. The method of claim 1 wherein the monitored fluorescence is normalized to the fluorescence monitored when the device is not contacted with a voltage and/or current source.

13. The method of claim 1 wherein the material layer comprises Europium Thenoyltrifluoroacetonate (EuTTA) distributed in PMMA.

14. The method of claim 12 wherein the material layer comprises Europium Thenoyltrifluoroacetonate (EuTTA) distributed in dPMMA.

15. The method of claim 14 wherein said layer includes about 0.5 to about 40 percent by weight of Europium Thenoyltrifluoroacetonate (EuTTA).

16. The method of claim 15 wherein the fluorescence intensity of the material layer varies with temperature as approximately a straight line with a slope of approximately $-0.05$/degree Celsius.

17. The method of claim 16 wherein said layer is illuminated with approximately 700 microwatts per centimeter squared of UV radiation in the wavelength range from 345 to 380 nanometers.

18. The method of claim 1 wherein said fluorescence is monitored using a CCD array.

19. The method of claim 10 wherein said fluorescence is monitored using a CCD array.

20. The method of claim 15 wherein said fluorescence is monitored using a CCD array.

21. The method of claim 20 wherein a thermal picture of substantially the entire device is imaged by a CCD array.

22. The method of claim 1 wherein said material layer comprises EuFOD distributed in a polymer.

23. The method of claim 22 wherein said layer includes about 2 to about 50 percent by weight of the EuFOD.

24. The method of claim 1, further comprising the step of producing a thermal transient in said device by delivering power, or increasing the delivery of power, to said device.

25. The method of claim 24 wherein said exposing step occurs substantially simultaneously with the onset of said thermal transient, and wherein the resulting fluorescence of said material is detected during said monitoring step.

26. The method of claim 24, wherein said exposing step occurs over a period of time which includes the duration of said thermal transient, and said monitoring step includes the step of gating a detector which detects the fluorescence of said material, substantially simultaneously with the onset of said thermal transient.

27. The method of claim 25 wherein said layer of fluorescent material has a fluorescence lifetime, $\tau$, which is smaller than $t_x$, the time required for heat to diffuse a preselected distance across the surface of said device, and wherein said exposing step occurs over a period of time less than $t_x$.

28. The method of claim 26 wherein said layer of fluorescent material has a fluorescence lifetime, $\tau$, which is smaller than $t_x$, the time required for heat to diffuse a preselected distance across the surface of said device, and wherein said detector is gated for a period of time less than $t_x$.

29. The method of claim 1 wherein said layer of fluorescent material has a fluorescence lifetime which is less than 10 nanoseconds.

30. The method of clainm 29 wherein said material comprises Rhodamine B distributed in polyethyleneimine.

31. The method of claim 29 wherein said material comprises bianthrone.

32. The method of claim 29 wherein said material comprises dimethylaminoazobenzene.

33. The method of claim 29 wherein said material comprises 9-methylanthracene.

34. The method of claim 1 wherein said device is an integrated circuit device.

35. The method of claim 1 wherein said device is a laser diode.

36. The method of claim 1 wherein said device is a Josephson junction device.

* * * * *